United States Patent [19]

McCoy et al.

[11] 4,044,118
[45] Aug. 23, 1977

[54] SOLUBILIZING PROCESS FOR OIL INSOLUBLE PESTICIDES

[75] Inventors: Frederick C. McCoy, Beacon, N.Y.; Carl Loyal W. Swanson, deceased, late of Hopewell Junction, N.Y., Viola C. Swanson, executrix

[73] Assignee: Texaco Inc., New York, N.Y.

[21] Appl. No.: 616,228

[22] Filed: Sept. 24, 1975

Related U.S. Application Data

[60] Division of Ser. No. 470,686, May 16, 1974, Pat. No. 3,939,272, which is a continuation-in-part of Ser. No. 275,680, July 27, 1972, Pat. No. 3,914,808.

[51] Int. Cl.$^2$ ............................................. A01N 9/36
[52] U.S. Cl. .............................. 424/200; 260/326 H; 424/346
[58] Field of Search ............................... 424/200, 346

[56] References Cited

U.S. PATENT DOCUMENTS

| | | | |
|---|---|---|---|
| 3,355,353 | 11/1967 | Jamison | 424/200 |
| 3,681,348 | 8/1972 | McCoy et al. | 71/93 X |
| 3,939,272 | 2/1976 | McCoy et al. | 424/276 |

OTHER PUBLICATIONS

Kirk–Othmer–Encyclopedia of Chem. Tech., vol. 1, p. 908 (1963).

*Primary Examiner*—Leonard Schenkman
*Attorney, Agent, or Firm*—Thomas H. Whaley; Carl G. Ries; Bernard Marlowe

[57] ABSTRACT

This invention concerns a process for converting normally oil-insoluble N-[1-halomethyl-1-(S-dialkylphosphorothioate)] methinyl phythalimide by treatment with alkylated phenols, and to the oil-soluble complexes resulting therefrom.

6 Claims, No Drawings

SOLUBILIZING PROCESS FOR OIL INSOLUBLE PESTICIDES

This is a division of application Ser. No. 470,686, filed May 16, 1974, now U.S. Pat. No. 3,939,272 which is a continuation-in-part of application Ser. No. 275,680, filed July 27, 1972, now U.S. Pat. No. 3,914,808.

This invention concerns a process for transforming certain pesticidal compounds normally insoluble in oil* to their oil-solubilized forms.

Oil-soluble as used herein refers to materials which do not possess sufficient solubility to permit the preparation of a clear 0.1% by weight solution of SAE 20 paraffin based oil at 75°–80° F.

More particularly, this invention relates to a process for converting a specific group of nitrogen-containing pesticides (described more fully below), which are normally insoluble in petroleum oils, to their oil-soluble form.

BACKGROUND OF THE INVENTION

As set forth in U.S. Pat. Nos. 3,681,348 and 3,914,308 the solubilization of noramlly oil-insoluble pesticidal substances is advantageous, since by rendering an additive soluble in a desired oily substrate, serious problems of non-homogeneity, sedimentation and unstable viscosities of the final composition are overcome. The latter difficulties are frequently encountered when dispersions of oil-insoluble pesticides, particularly anti-fungal agents, are prepared for application to vegetation.

As is well known, anti-fungal agents are used to inhibit or to control the growth of fungi. The need for oil-soluble anti-fungal substances is especially pressing in the treatment of plants in tropical or sub-tropical climates, or in the application of the more highly toxic agricultural pesticides. For example, in the aforementioned climates, humidity is high and inhibiting the growth of fungi is difficult. This high humidity, combined with frequent rainfall, may remove an anti-fungal completely or render it ineffectual for protective purposes. This necessitates more frequent applications of anti-fungal which, in addition to being troublesome and costly, makes it difficult to control the growth of the fungus being treated, particularly if the anti-fungal has phytotoxic properties.

** Pesticides as defined herein include anti-fungal agents herbicides, and plant growth regulators.

In view of the above problems, particularly in the application of anti-fungals in areas of high humidity and high rainfall, there is a need for a process to transform these normally oil-insoluble nitrogen-containing pesticidal substances into oil-soluble forms.

Recently it has been found through trial and error that the process disclosed in U.S. Pat. No. 3,681,348 can be extended to certain other oil-insoluble nitrogen-containing pesticidal agents to yield stable, useful oil-soluble complexes.

SUMMARY OF THE INVENTION

In practice, a normally oil-insoluble nitrogen containing agent to be converted to its oil-soluble form is admixed with at least a molar excess of at least one alkylated phenol-type compound to form a fluid mixture, and the mixing is continued until a substantially clear solution is obtained. The solution can be stored as is or any insoluble particles can be separated prior to storage or use.

In one favored process the above agents which are normally insoluble in petroleum based oils are admixed with a molar excess ranging from 2:1 to 20:1 of at least one hydroxylate benzene nucleus alkylated with alkyl groups containing from 6 to 12 carbon atoms, in the presence of sufficient inert solvent to provide a fluid, easily stirred mixture, then continuing said mixing at temperatures ranging between 40° to 100° C until substantial solubilization of the compound takes place and a substantially clear solution is obtained. Again the solution may be clarified (by filtration) or not, concentrated or diluted for subsequent use.

In another favored variation, each part by weight of the oil-insoluble material to be solubilized is contacted at 40° to 100° C, with 1 to 20 parts by weight of the alkylated phenol solubilizer and 2 to 80 parts by weight mixture of paraffinic oils and the mixture is agitated while heating until a clear homogeneous concentrate is formed.

In order to more clearly set forth the scope of the subject invention the following additional disclosure is submitted:

A. Alkylated Phenol Type Compound.

This is the generic designation used to define the agents which solubilize the normally oil-insoluble substances. These solubilizing agents are chosen from the mono and dinuclear aromatics that contain at least one alkylating group and at least one hydroxyl group. The alkylating group or groups can contain a total of between 3 and 100 carbon atoms, desirable from 3 to 30 carbon atoms and perferably from 6 to 200 carbon atoms. The alkylating groups can be arranged in either branched chains or straight chains although branched chains are preferred. The alkylated phenol-type compound can be in the form of relatively pure, discrete single compounds or in the form of blends or mixtures. Depending upon their physical state, solid or liquid, or the convenience of the user, the solubilizing compounds can be used with or without relatively low boiling inert solvents to assist in the solubilization process. These solvents, which are usually removed in a subsequent stripping operation, are described infra.

Illustrative of the favored class of solubilizing agents and the alkylated hydroxy mononuclear phenols, cresols and the like, such as the butyl phenols, the pentyl phenols, the hexyl phenols, the heptyl phenols, the octyl phenols, the nonyl phenols, the decyl phenols, the undecyl phenols, the dodecyl phenols, the tridecyl phenols, their mixtures, particularly where the alkylating groups on the phenols contain from 6 to 12 carbon atoms and are branched rather than straight chain.

B. Conditions Required for Oil-Solubilization.

1. Admixing Reactants — Generally speaking, the admixture required for forming the solubilization mixture can utilize any device capable of producing a homogeneous mixture. These include stirring devices, blending devices, mills, etc. No particular order of addition is required for operability. When the components are both liquids the usual procedure is to form a mixture of the normally oil-insoluble pesticidal nitrogen-containing compound and a molar excess of alkylated phenol-type compound until the solution substantially clears, indicating that substantial solubilization has taken place.

2. Temperature and Pressure — Ordinarily ambient temperatures (i.e. between 20°–30° C) are satisfactory for admixing the components of the mixture. To effect even more rapid solubilization and formation of the oil-soluble complexes both the alkylated phenol and the pesticidal compound to be solubilized are heated together with or without agitation until they blend. Ordinarily no advantage accrues in using temperatures below about 20°–30° C so that temperatures ranging from 20° C and up are normally employed. The limiting factors in employing relatively high temperatures (i.e. above 100° C) are the stability of said pesticidal component and/or the volatility of inert solvents that may be used. Volatility can be controlled by the use of a pressurized system but because of increased cost and operating hazards the usual practice is to use atmospheric pressures and temperatures not exceeding 100° C.

3. Relatively Low-Boiling Inert Solvent — As indicated earlier, the use of one or more inert solvents boiling under 100° C is desirable where difficulty is encountered in obtaining dissolution of the pesticides in the alkylphenol. Generally speaking, most solvents or mixtures of solvents inert to reacting with one or both components, and sufficiently low-boiling to permit their ready removal by distillation at temperatures not exceeding 100° C can be employed. When inert solvents are employed they can form up to about 70% of the final mixture weight. These solvents can be stripped off using conventional atmospheric or vacuum distillation, or the blends containing them can be kept in the unconcentrated form. Illustrative solvents are benzene, toluene, ketones such as acetone, methyl ethyl ketone, the cellosolves and mixtures of these solvents.

4. Solubilization Times — The time required for preparation of the oil-insoluble form of the normally oil-insoluble compound cannot be stated with precision since it is dependent upon variables such as the nature of the oil-insoluble compound, the nature of the alkylated phenol-type compound, temperature employed and/or whether inert solvent is used. In some instances a clear, solvent-free concentrate can be attained in 10 minutes to ½ hour while in other cases as much as 2–3 hours or more are required. Most solubilization takes place within 1 to 2 hours.

5. Types of Oil used for Dilution. Generally speaking any mineral oil of suitable viscosity for use as a conventional agricultural spray oil can be used. These include naphthenic, paraffinic and certain types of asphaltic oils having Saybolt viscosities at 100° F from about 30–400 seconds. The preferred compositions for use with the insoluble pesticides are mixtures containing from about 0.1 to 20% by weight of pesticide in paraffinic oils having SUS viscosities of 50 to 100 at 100° F and having an aromatic content of less than about 8%.

6. Ratio of Phenol-Type Compound to Insoluble Pesticides. — A molar excess of the phenol-type solubilizating agent is desirable. The exact excess required is a variable dependent upon the substance being solubilized and by the minimum amount of "phenol" required to achieve satisfactory solubilization. In most instances molar ratios of about 2:1 to 20:1 and higher of solubilizing agent to insoluble material will suffice with a narrower range of about 2:1 to 4:1 being preferred.

7. Preparation of Oil Solutions of Solubilized Compounds. — After the complexes of alkylated phenol-type compounds and solubilized compounds are prepared they may be incorporated in oil by any of the conventional methods used in blending oil base compositions. For instance, the concentrate of solubilized compounds plus oil may be heated to 40° to 60° C with mechanical agitation for 15 minutes or more until a clear blend is achieved.

8. Preferred Oil-Soluble Compositions. — While a broad range of alkylated phenol-type solubilizing agents can be used, the favored group comprise the alkylated hydroxy mononuclear aromatics commonly referred to as "alkylphenols". Within this relatively narrow class, the preferred solubilizers are those mono-hydroxylated benzenes alkylated with alkyl groups containing from 6 to 20 carbon atoms, preferably branched. These compositions comprise from 25 to 95 parts by weight of these solubilizing agents and from 75 to 5 parts by weight of one or more pesticidal materials lacking the necessary solubility in oil. These are preferred because they are effective against many infestations in plants.

9. Compounding Oil-Based Pesticidal Compositions. — Since the solubilized pesticidal agents of this invention have solubility in petroleum-derived solvents they may be incorporated into a convenient petroleum-derived solvent in concentrations sufficient to achieve the desired effective control. Alternately, they may be used as is, without further oil dilution. When the oil-soluble material is diluted with oil, the concentration of pesticide plus solubilizer employed depends upon the particular agent or agents used, the effect desired and the adjuvants accompanying the other ingredients. Ordinarily, amounts ranging from about 0.1 to 10% by weight of pesticidal plus solubilizer are used, the remainder being oil. High concentrations up to 50% or more may be used if desired. The lower range referred to supra in most instances constitutes an effective concentration. The above pesticidal agents are often accompanied by one or more pesticidal adjuvants which comprise from 0 to 10% by weight of the total pesticidal composition. The optional agents used to condition, modify or enhance the desired pesticidal effect include such petroleum-soluble adjuvants as, for example, Malathion, DDT and numerous other products known in the technical* and patent literature. Also included as adjuvants are potentiators or synergists typified by piperonyl butoxide, Sesoxane [2-(3,4-methylenedioxyphenoxy)-3,6,9-trioxoundecane], sulfoxide (n-octyl sulfoxide or isosafrole), n-propyl isome, sesame oil extractives, octachlorodipropyl ethers, etc. The formulation of the compositions can be achieved by vigorously blending, mixing or stirring the solubilized anti-fungal plus solubilizer in a petroleum-based oil such as a highly refined paraffinic based oil having an aromatic content of less than about 8%, a viscosity SSU at 100° F of about 100, at temperatures ranging from about 40° to 100° C until a substantially homogeneous mixture is achieved. These compositions can be sprayed or fogged using conventional equipment for applying liquids including hand and machine operated sprayers, from the air or from the ground.

* See for example "Pesticidal Index", compiled and edited by E. H. Frear, 3rd Edition, published by College Science Published, P.O. Box 798, State College, Pa.

10. Oil-Insoluble, Nitrogen-Containing Pesticides. The normally oil-insoluble pesticides which lend themselves to solubilization by the inventive process are selected from the group consisting of 5,6-dihydro-2-lower alkyl1,4-oxathiin-3-carboxanilide-4,4-dioxides(-Plantvax**), wherein the lower alkyl radical contains 1 to 4 carbon atoms preferably 1 (one), N-(2-alkylidine) aminoguanidines wherein the alkyl moiety contains 7 to 15 carbon atoms preferably where the 2-alkylidine is undecylidine, methyl 1-(butylcarbamoyl)-2-benzamidazole carbamate (Benlate)* and N-[1-halomethyl- 1-[-S-dialkylphosphorodithioate]] methinyl phthalimide, wherein the alkyl contains 1 or 2 carbon atoms.
** Registered trademark of Uniroyal
* Registered trademark of Dupont All of the above group of compounds are known and their preparation is described in the literature.

The formulas of the favored members of the group are given below:

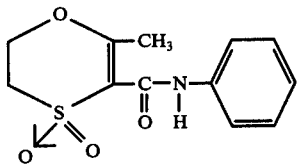

5,6-dihydro-2-methyl-1,4-oxathiin-3-carboxanilide-4,4-dioxide(Plantvax).

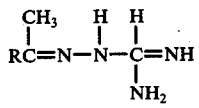

N-(2-alkylidine) amino guanidines (where R is an alkyl radical of from 6-14 carbons).

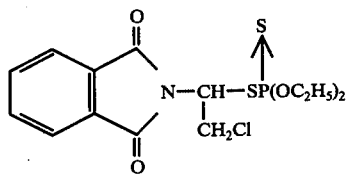

N-1-chloromethyl-1-[S-diethylphosphorodithioate] methinyl phthalimide. (Torak)**
** Registered trademark of Hercules, Inc.

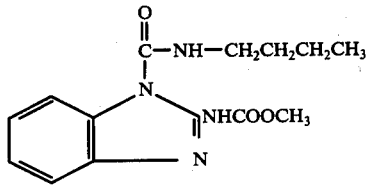

methyl 1-(butylcarbamoyl)-2-benzimidazole carbamate (Benlate)

In order to disclose the invention in the greatest possible detail, the following illustrative examples are given.

EXAMPLE 1

Solubilization of N-(2-Undecyoidine) Aminoguanidine using one Process Embodiment of this Invention A 300 parts by weight portion of nonylphenol, 150 parts by weight of N-(2-undecylidine) aminoguanidine and 370 parts by weight mixture of paraffinic oil having a viscosity of approximately 80 S.U.S. at 100° F are stirred and heated to 150° F for about 2 hours until a clear homogeneous concentrate is formed.

In the absense of the nonylphenol solubilizer, the aminoguanidine is soluble in the mineral oil to the extent of less than 0.1% at room temperature.

The above concentrate of N-(2-undecylidine) aminoguanidine when applied at a concentration of 0.275% by weight of the oil concentrate (500 ppm of active agent) effectively controlled Helminthsporium leaf spot in rice. At double this concentration (1000 ppm of active agent) control of coffee rust fungus was observed.

EXAMPLE 2

Solubilization of N-(2-undecylidine) Aminoguanidine using another Process Embodiment A 300 parts by weight portion of nonylphenol and 150 parts by weight of N-(2-undecylidine) aminoguanidine are stirred and heated to 60° to 70° C with about 500 parts by weight of benzene to give a clear solution. The solution is filtered to remove traces of insoluble material. The filtrate contains the solubilized N-(2-undecylidine) aminoguanidine. The inert solvent (benzene) is evaporated off to produce a clear concentrated solution which can be stored or diluted with paraffinic oil. When the concentrate is blended at 50° C with a refined paraffinic oil (having an API gravity of 28.0-31.0 and S.U.S. viscosity at 100° F of 325-335) a clear solution is obtained which remains clear on cooling to room temperature.

In very similar runs solubilization of the above "aminoguanidine" in the above oil is effected employing 150 parts by weight of dodecyl phenol which is a phenol alkylate with $C_{12}$ alkyl groups. Again an oil-soluble clear concentrate is obtained.

In another related run 150 parts by weight of pentadecyl phenol (a phenol alkylated with a $C_{15}$ olefin is used as the solubilizing agent. Again an oil-soluble clear concentrate is obtained.

EXAMPLES 3 TO 5

Solubilization of other Oil-Insoluble N-(2-Alkylidine) Aminoguanidines

Using the same quantities of nonylphenol and the same process conditions and procedure disclosed in Example 1, the solubilizing process is repeated except that in Example, 3, 100 parts by weight of N-(2-heptylidine) aminoguanidine is substituted for the "undecylidine" substituent of Example 1. The same solubilizing effect is observed. In the same vein Example 4 shows the solubilization of 100 parts by weight of N-(2-pentadecylidine) aminoguanidine using 300 parts by weight on nonylphenol and in Example 5 the solubilization of N-(2-tridecylidine) aminoguanidine is accomplished using 300 parts by weight of nonylphenol. In all 3 examples the same quantity and type of oil that is used in Example 1 is employed.

EXAMPLE 6

Solubilization of the Compound of Example 1, using another Phenol-type Compound and the same Paraffinic Oil A 350 parts by weight portion of dodecyl phenol is blended in a stirred beaker with 100 parts by weight of N-(2-undecylidine) aminoguanidine and 350 parts by weight of the paraffinic oil of Example 1. As in Example 1 activity is observed against Helminthsporium in rice at concentrations of 1000 ppm of the active agent.

EXAMPLES 7 AND 8

Solubilization of 5,6-Dihydro-2-Methyl-1,4-Oxathiin-3-Carboxanilide-4,4-Dioxide without Solvent A 60 parts by weight portion of the above compound is mixed with 140 parts by weight of nonylphenol for 2 hours at 70° C and filtered to remove any insoluble matter. The filtrate can be stored in concentrated form or diluted with paraffinic oils having S.U.S. viscosities at 100° F of 50 to 100 to give stable oil-based solutions. Without solubilizing treatment, a stable solution of 0.1% by weight in the above paraffinic oils cannot be prepared.

Using the same procedures, relative ratios of ingredients, a 30% by weight solution of 5,6-dihydro-2-n-propyl-1,4-oxathiin-3-carboxanilide-4,4-dioxide in nonylphenol is prepared and diluted with the above paraffinic oil to produce a 2.51% by weight solution which is stable to storage at room temperature.

EXAMPLE 9

Solubilization of 5,6-Dihydro-2-Methyl-1,4-Oxathiin-3-Carboxanilide-4,4-Dioxide using Aromatic Solvent for Initial Solubilization A 60 parts by weight portion of the above compound, 140 parts by weight of nonylphenol and 100 parts by weight of benzene are heated to 55°–65° C with stirring to produce a clear solution which remains clear on cooling to room temperature. To the benzene solution are added 300 parts by weight of paraffinic oil having a viscosity of about 100 S.U.S. at 100° F. The benzene is stripped off, leaving a clear concentrate containing 12% active ingredient by weight.

EXAMPLE 10

Solubilization of 5,6-Dihydro-2-Methyl-1,4-Oxathiin-3-Carboxanilide-4,4-Dioxide incorporating Paraffinic Oil into the Solubilizing System A 140 parts by weight portion of nonylphenol, 60 parts by weight of the "Dioxide" and 150 parts by weight of paraffinic oil having a viscosity of about 100 S.U.S. at 100° F are stirred and heated to 65°–75° for about 4 hours until a clear homogeneous concentrate is formed.

In the absence of nonylphenol, a stable 0.1% by weight solution of the "Dioxide" in paraffinic oil cannot be prepared.

EXAMPLE 11

Solubilization of 5,6-Dihydro-2-Methyl-1,4-Oxathiin-3-Carboxylate-4,4-Dioxide using different Alkylated Phenols Using the procedure of Example 7 and 8 and 60 parts by weight of the "Dioxide", the following portions of alkylated phenols are substituted for nonylphenol as solubilizer. The temperature is maintained at 60° to 70° C during the solubilization process of 1 hour.

| EXAMPLES | ALKYLATED PHENOL | PARTS BY WEIGHT |
|---|---|---|
| 12 | equi-weight mixture of nonylphenol and dodecylphenol | 200 (100:100) |
| 13 | dodecylphenol | 180 |

In all instances clear stable solutions are obtained.

EXAMPLE 14

Solubilization of Torak*

A 1 g. portion of Torak insecticide and 19 g. of nonylphenol are heated until a clear solution is prepared. A 2.5 g. portion of this solution and 42.5 g. of mineral oil are blended at room temperature resulting in a clear solution.

*N-1-chloromethyl-1-[S-diethylphosphorodithioate]methinyl phthalimide

EXAMPLE 15

Solubilization of Methyl 1-(Butylcarbamyl)-2-Benzimidazole Carbamate 56 g. Benlate fungicide containing 50% methyl 1-(butylcarbamoyl)-2-benzimidazole carbamate and 50% inert material were stirred at 140° F with three separate 200 ml portions of benzene. After filtering, the benzene filtrates were combined and 532 g. nonylphenol added. The benzene was stripped leaving 560 g. clear, viscous concentrate.

When blends of 2% and 5% by weight of this concentrate were made in a paraffinic mineral agricultural spray oil, no crystal separation was observed after 48 hours standing.

As the preceding disclosure indicates numerous changes, substitutions and modifications can be made in this invention without departing from the inventive process. The metes and bounds of this invention are best determined by reading the following claims in light of this specification.

What is claimed is:

1. A process for converting a normally oil-insoluble N-[1-halomethyl-1-(S-dialkylphosphorodithioate)]methinyl phythalimide pesticide wherein said alkyl group of said dialkylphosphorothioate contains 1 to 2 carbon atoms, to their oil-soluble form by:
   a. admixing each mole of said pesticide to be converted to oil-soluble form with:
   b. a molar excess of at least one alkylate phenol wherein the alkyl substituent contains from 3 to 30 carbon atoms, at temperatures ranging from about 20° C to 100° C, until said normally oil-insoluble compounds are converted to their oil-soluble form.

2. The process of claim 1 wherein the process is conducted in the presence of an inert solvent.

3. The process of claim 2 wherein the inert solvent is aromatic.

4. A process for converting N-[1-chloromethyl-1-(S-dialkylphosphorodithioate)] methyinyl phthalimide compounds, wherein the alkyl group of said dialkylphosphorodithioate contains 1 to 2 carbon atoms, which are normally insoluble in petroleum based oils to a petroleum based oil-soluble concentrate form, consisting essentially of:
   a. admixing each part by weight of the compounds to be solubilized in petroleum based oils with:
   b. from about 2 to 20 moles of an alkylated phenol containing from 3 to 30 carbon atoms in the alkyl group at temperatures ranging from 20° to 100° C.
   c. until a petroleum based oil-soluble concentrate form is obtained.

5. A process for converting a normally oil-insoluble pesticidal compound N-(1-chloromethyl-1-(S-dialkylphosphorodithioate) methinyl phthalimide, wherein the alkyl group of said dialkylphosphorothioate contains 1 to 2 carbon atoms, to their paraffinic oil-soluble concentrated forms consisting essentially of admixing each part by weight of said oil-soluble compound with from 1 to 20 parts by weight of at least one alkylated phenol wherein the alkyl substituent contains from 3 to 30 carbon atoms, and 1 to 50 parts by weight of paraffinic oils having Saybolt viscosities at 100° F from 30 to 400 seconds, while maintaining the temperature between about 20° to 100° C until said paraffinic oil-based concentrate is formed.

6. A paraffinic oil-soluble pesticide concentrate of a N-[1-chloromethyl-1-(S-dialkylphosphorodithioate)] methyinyl phthalimide compound, wherein the alkyl group of said dialkylphorodithioate contains 1 to 2 carbon atoms, consisting essentially of:
   a. from about 25 to 95 parts by weight of a phenol alkylated with alkyl groups containing 3 to 30 carbon atoms, and
   b. from about 75 to 5 parts by weight of said pesticide.

* * * * *